US011154266B2

(12) United States Patent
Radicke

(10) Patent No.: US 11,154,266 B2
(45) Date of Patent: Oct. 26, 2021

(54) GENERATING A RESULT IMAGE

(71) Applicant: Siemens Healthcare GmbH, Erlangen (DE)

(72) Inventor: Marcus Radicke, Veitsbronn (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/574,646

(22) Filed: Sep. 18, 2019

(65) Prior Publication Data

US 2020/0100753 A1  Apr. 2, 2020

(30) Foreign Application Priority Data

Sep. 27, 2018 (EP) ..................................... 18197212

(51) Int. Cl.
*A61B 6/00* (2006.01)
*A61B 6/02* (2006.01)

(52) U.S. Cl.
CPC ............ *A61B 6/5205* (2013.01); *A61B 6/025* (2013.01); *A61B 6/4007* (2013.01); *A61B 6/586* (2013.01)

(58) Field of Classification Search
CPC ......... A61B 6/586; A61B 6/00; A61B 6/4007; A61B 6/4014; A61B 6/4417; A61B 6/4441; A61B 6/4464; A61B 6/4488; A61B 6/56; A61B 6/025; A61B 6/5205; H05G 1/70; H05G 1/32; H05G 1/60; G21K 1/065
See application file for complete search history.

(56) References Cited

U.S. PATENT DOCUMENTS

| 2005/0063513 | A1* | 3/2005 | Hsieh | A61B 6/585 378/98.8 |
| 2011/0129067 | A1 | 6/2011 | Fukuwara | |
| 2011/0170667 | A1* | 7/2011 | Ruggiero | A61B 6/461 378/98.5 |
| 2016/0181053 | A1* | 6/2016 | Wang | A61B 6/105 378/41 |
| 2016/0374187 | A1 | 12/2016 | Lai | |
| 2018/0098740 | A1* | 4/2018 | Brunner | G16H 30/20 |
| 2018/0144465 | A1* | 5/2018 | Hsieh | G06N 3/08 |

FOREIGN PATENT DOCUMENTS

DE    102010011662 A1    9/2011
DE    102010011663 A1    9/2011

OTHER PUBLICATIONS

Extended European Search Report and English translation thereof dated Mar. 29, 2019.
Extended European Search Report for European Patent Application No. 18197212.6 dated Mar. 29, 2019.

* cited by examiner

*Primary Examiner* — Joanne M Hoffman
*Assistant Examiner* — Alexei Bykhovski
(74) *Attorney, Agent, or Firm* — Harness, Dickey & Pierce, P.L.C.

(57) ABSTRACT

A method is for generating a result image using a tomosynthesis device including a plurality of stationary X-ray sources. In an embodiment, the method includes detecting at least one faulty X-ray source among the plurality of stationary X-ray sources; adapting a reconstruction to compensate for the faulty X-ray source; and generating the result image using the reconstruction adapted.

23 Claims, 2 Drawing Sheets

GENERATING A RESULT IMAGE

PRIORITY STATEMENT

The present application hereby claims priority under 35 U.S.C. § 119 to European patent application number EP 18197212.6 filed Sep. 27, 2018, the entire contents of each of which are hereby incorporated herein by reference.

FIELD

Embodiments of the invention generally relate to a method for generating a result image using a tomosynthesis device, to a compensation device, to a tomosynthesis device and to a tomosynthesis system.

BACKGROUND

Medical examinations of a breast, in particular those of a human female breast, are typically carried out to enable malignant changes in the breast tissue to be identified or diagnosed in a reliable and targeted manner. One current method to enable such an examination to be carried out is mammography.

A conventional mammography device comprises an X-ray source arranged on a frame, a detector unit and a compression unit. A U-shaped carrier that has the X-ray source arranged at one of its ends and the detector unit at the other is secured rotatably on the frame. Before an examination, the breast is usually compressed via a compression element. In the case of a cranio-caudal projection, or in the case of a mediolateral oblique projection, the carrier is oriented vertically in the first instance, and is inclined by for example 45 degrees for capturing the second image. During changing between the projections, the U-shaped carrier is pivoted about its central axis.

In addition to conventional mammography, tomosynthesis is gaining in importance. In tomosynthesis, the detector, with the compression unit, is uncoupled from the central U-shaped carrier. In this examination method, the compressed breast is held stationary and irradiated from different directions by an X-ray source, which for example travels along an arcuate segment. The individual projection images that are acquired in this way are temporarily stored in a processor unit and then reconstructed to give a volume image.

The 2D X-ray images in mammography enable good diagnosis. However, the usefulness of the findings in a mammography image reaches its limit when different tissue layers are overlaid in the direction of the X-ray beam, or the tissue is very dense. Typically, it is only possible to a limited extent to draw a conclusion about the position of details in the direction of radiation. 3D imaging is brought in to minimize these restrictions.

Unlike a 3D computed tomogram, tomosynthesis makes use of a restricted angular range during the acquisition. In tomosynthesis, the X-ray source moves around the breast, for example along an arcuate section. As a result of the predetermined principal beam direction of the X-ray source, which moves on a predetermined path, structures in the principal beam direction may be blurred.

There are now known in the art tomosynthesis systems having a plurality of X-ray sources that are arranged stationary within a field in the form of a matrix, in rows and columns. A control unit controls the X-ray sources of the field such that the X-ray sources emit X-ray beams successively, in dependence on their row and column in the field. Then, an overall volume image is calculated from the individual projection images that have been acquired in this way, in the context of a reconstruction method.

SUMMARY

The inventors have discovered that in the method described above, it is disadvantageous that as soon as one of the X-ray sources is no longer fully functional the method can no longer be used.

At least one embodiment of the present application reduces the down times during operation of a tomosynthesis device having a plurality of stationary X-ray sources.

Embodiments of the present application are directed to a method for generating a result image using a tomosynthesis device, a compensation device, a tomosynthesis device, and a tomosynthesis system.

The method of at least one embodiment serves to generate a result image using a tomosynthesis device that has a plurality of stationary X-ray sources. Here, the method of at least one embodiment includes at least: at least one faulty X-ray source is detected, a reconstruction is adapted for the purpose of compensating for the faulty X-ray source, and the result image is generated by way of the adapted reconstruction.

At least one embodiment is directed to method for generating a result image using a tomosynthesis device including a plurality of stationary X-ray sources, the method comprising:

detecting at least one faulty X-ray source among the plurality of stationary X-ray sources;

adapting a reconstruction to compensate for the faulty X-ray source; and generating the result image using the reconstruction adapted.

The compensation device serves to compensate for a faulty X-ray source in a tomosynthesis device having a plurality of stationary X-ray sources. It includes a controller having a detection unit that is embodied for detecting a faulty X-ray source. The compensation device further includes an adaptation unit that is embodied for adapting a reconstruction for the purpose of compensating for the faulty X-ray source, and a reconstruction unit that is embodied for generating a result image by way of the adapted reconstruction.

At least one embodiment is directed to a compensation device for a tomosynthesis device including a plurality of stationary X-ray sources, the compensation device comprising:

a controller including a detection unit embodied to detect a faulty X-ray source among the plurality of stationary X-ray sources;

an adaptation unit embodied to adapt a reconstruction to compensate for the faulty X-ray source; and a reconstruction unit embodied to generate a result image using the reconstruction adapted.

Thus, in the context of at least one embodiment of the invention the controller, the adaptation unit and the reconstruction unit cooperate and together include, as the compensation device, all the components for carrying out a method according to at least one embodiment of the invention for generating a result image.

Components of the compensation device according to at least one embodiment of the invention may predominantly be embodied as software components. In principle, however, some of these components may also be realized in the form of software-supported hardware, for example FPGAs or similar, in particular when particularly fast calculations are called for. Likewise, the required interfaces may be embodied as software interfaces, for example if all that needs to be done is to take over data from other software components. However, they may also be embodied as hardware interfaces that are controlled by suitable software.

In particular, the compensation device according to at least one embodiment of the invention may be part of a user terminal of a tomosynthesis device.

At least one embodiment is directed to a tomosynthesis device, comprising:
  a plurality of X-ray sources; and
  a compensation device including
    a detector to detect a faulty X-ray source among the plurality of X-ray sources, and
    at least one processor to
      adapt a reconstruction to compensate for the faulty X-ray source, and
      generate a result image using the reconstruction adapted.

Realization in a largely software form has the advantage that it is also possible to retrofit compensation devices that have already been in use with a software update in a simple manner, such that they operate in an inventive manner. Thus, at least one embodiment is directed to a computer program product having a computer program that may be loaded directly into a storage device of a compensation device of a tomosynthesis device and has program portions, in order to carry out all the steps of the method according to at least one embodiment of the invention when the program is executed in the compensation device. A computer program product of this kind may include, in addition to the computer program, where appropriate additional constituent parts such as documentation and/or additional components, and hardware components such as hardware keys (dongles, etc.) for utilizing the software.

BRIEF DESCRIPTION OF THE DRAWINGS

The invention will be explained again in more detail below by way of the attached figures and with reference to example embodiments. Here, like components are provided with identical reference numerals in the different figures. As a rule, the figures are not to scale. In the figures.

DETAILED DESCRIPTION OF THE EXAMPLE EMBODIMENTS

Figure 1:
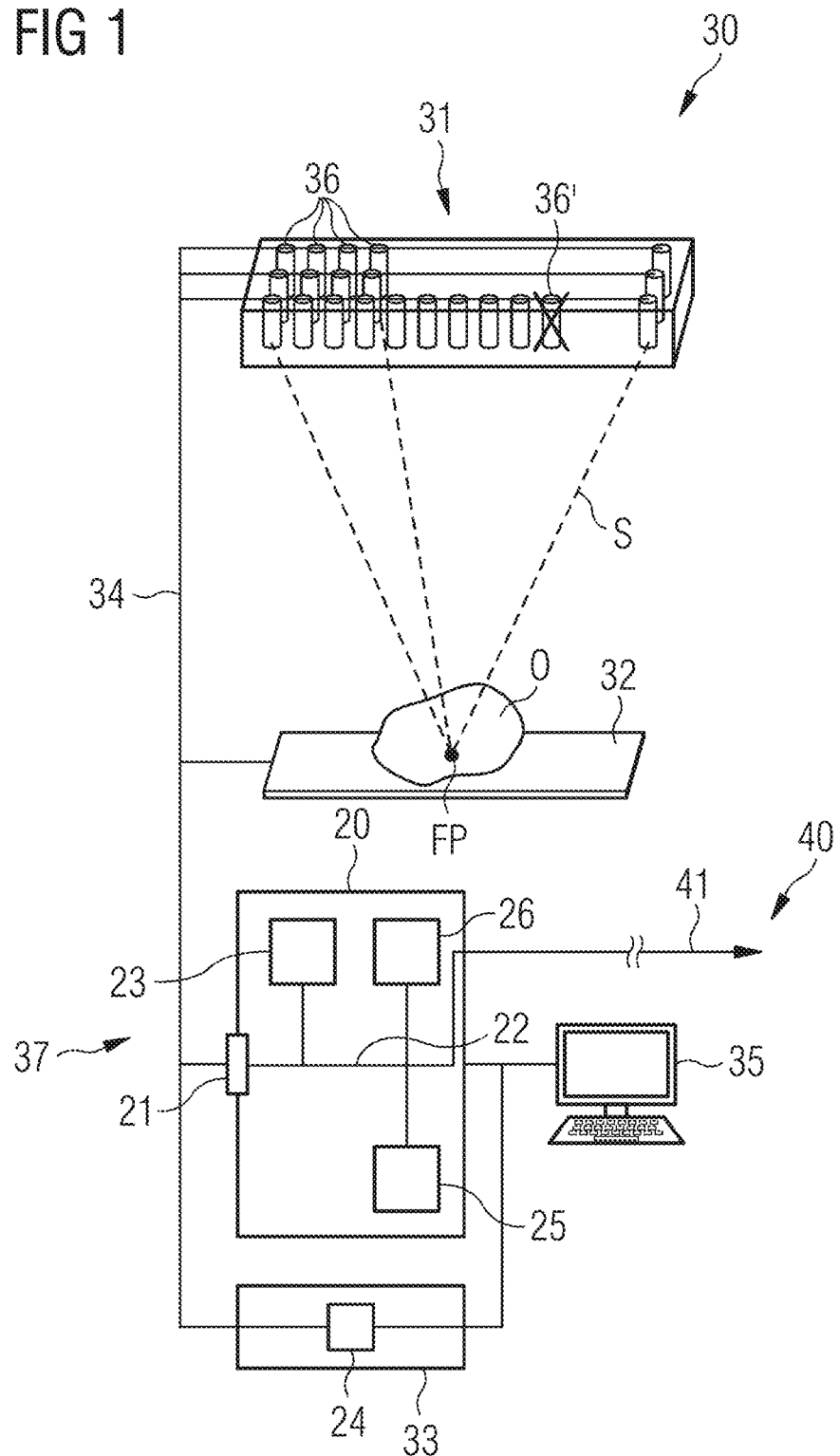
FIG. 1 shows a rough schematic illustration of an example embodiment of a tomosynthesis system according to the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method of at least one embodiment serves to generate a result image using a tomosynthesis device that has a plurality of stationary X-ray sources. Here, the method of at least one embodiment includes at least: at least one faulty X-ray source is detected, a reconstruction is adapted for the purpose of compensating for the faulty X-ray source, and the result image is generated by way of the adapted reconstruction.

The result image is any desired image that may be generated via a tomosynthesis device. It may be two-dimensional or three-dimensional. In this context, the result image is usually reconstructed from a number of projection images. Here, each respective projection image is for example acquired from a respective direction as described in the introduction, using a respective one of the stationary X-ray sources, which are preferably arranged in a matrix. In the context of dual- or multi-energy imaging, however, it is also possible for a plurality of projection images to be activated, with different energy spectra of the X-ray radiation from a respective direction. The result image may for example be reconstructed in the form of a synthetic mammogram and/or as a volume image, for example in the form of a layered image data stack, via methods known in the art.

Here, the term "reconstruction" indicates a reconstruction procedure or a reconstruction method. Thus, reconstruction designates a partial procedure in the generation of the result image, in which the projection images, which were acquired previously from different angles, are used in conjunction with information on their angles as input data to determine the result image.

In a regular reconstruction, there is available a complete or normal set of projection images that have been acquired from all the projection directions provided for a defined examination, or using all the correspondingly required X-ray sources.

If, however—as in the case of at least one embodiment of the invention—one of the X-ray sources is faulty, it is not possible to acquire a projection image that is suitable or equally valid, or indeed any projection image at all, from the direction of this X-ray source, or to use it as input data for the reconstruction. For this reason, according to at least one embodiment of the invention only an imperfect set of projection images serving as the basis for the reconstruction is available.

Thus, at least one embodiment of the invention does not relate to a normal or regular tomosynthesis method using a plurality of stationary X-ray sources as in the prior art, but to a method that differs from this because of at least one faulty, not fully functional X-ray source.

The at least one faulty X-ray source is detected or determined—that is to say a functional deviation or a defect in the X-ray sources is identified. This may be performed for example by measuring a drop in performance or a resistance measurement at the X-ray sources. As an alternative or in addition, the X-ray sources may be compared in the course of a calibration measurement, and in this way deviations in individual X-ray sources may be identified.

The concept of detecting "at least one" faulty X-ray source means that it is also possible for there to be any (small) number—that is to say for example also two, three, four, five or more—faulty X-ray sources. In this context, depending on the application, the question of the maximum number of faulty X-ray sources that still give a sufficient level of quality in the generated result image for a useful finding has to be evaluated.

Here, the term "adaptation of the reconstruction" is understood to mean a change from a normal reconstruction wherein the input data were acquired in the regular manner provided for examination, via a fully functional tomosynthesis device. The adaptation is made here in particular in dependence on the detected faulty X-ray source in order to compensate for the effect thereof on the imaging. That is to say that according to the invention the negative effect that the faulty X-ray source would have on the imaging is reduced to the greatest possible extent by adapting the reconstruction. In the course of adapting the reconstruction, for example basic elements of the method, such as a filtered back projection (FBP) suitable for the tomosynthesis or the like may be selected. Further, where required pre- or post-processing steps may be carried out as appropriate. However, it is also possible to adapt a plurality of parameters, such as the weighting of individual projection images.

Generating the result image may be performed with a temporal and/or spatial offset for the purpose of adapting the reconstruction. That is to say that, in the course of adapting the reconstruction, procedures, settings and/or parameter values can be determined that are used later, or with a temporal offset, and/or at a different location or in a spatially separated reconstruction unit in the course of reconstruction. However, generating the result image may also be performed directly after the previous method steps and/or in a processor unit in which the adaptation unit and reconstruction unit and/or controller are integrated.

The compensation device serves to compensate for a faulty X-ray source in a tomosynthesis device having a plurality of stationary X-ray sources. It includes a controller having a detection unit that is embodied for detecting a faulty X-ray source. The compensation device further includes an adaptation unit that is embodied for adapting a reconstruction for the purpose of compensating for the faulty X-ray source, and a reconstruction unit that is embodied for generating a result image by way of the adapted reconstruction.

Thus, in the context of at least one embodiment of the invention the controller, the adaptation unit and the reconstruction unit cooperate and together include, as the compensation device, all the components for carrying out a method according to at least one embodiment of the invention for generating a result image.

The tomosynthesis device has a plurality of stationary X-ray sources and a compensation device according to at least one embodiment of the invention, and these serve to acquire projection images. Here, the term "plurality" means at least more than one X-ray source but also at least more X-ray sources than are necessary for imaging that meets the demands of a useful finding. Thus, the tomosynthesis device has for example 25 tubes of X-ray sources. Where there are lower demands, imaging for example with at least half the originally provided X-ray sources would also be possible.

The X-ray sources are stationary, or fixed. That is to say that they are arranged, at least during an examination, unmoving in relation to an object undergoing examination, such as a patient, and in particular in an array or a matrix, unmoving in relation to one another. Possible X-ray sources are in principle any suitable—that is to say sufficiently small—X-ray sources. They may for example be embodied as field emitter tubes, in particular in the form of carbon nanotubes.

The tomosynthesis system includes a tomosynthesis device according to at least one embodiment of the invention and a reconstruction device according to at least one embodiment of the invention. In addition, it may have further components such as an interface with a network. Moreover, for example data relating to the faulty X-ray source may be transmitted. As a result, where appropriate service staff who can perform a repair or replacement of the defective X-ray source may be informed automatically. The data may, however, also be utilized for example only to carry out examinations with lower demands of quality of the imaging on the no longer fully functional tomosynthesis device until repair or overhaul is carried out, and reallocate examinations that make higher demands.

The compensation device according to at least one embodiment of the invention may advantageously be retrofitted in already existing tomosynthesis devices. It is likewise possible to equip tomosynthesis devices that are to be newly manufactured with the compensation device according to at least one embodiment of the invention already at the time of manufacture, however.

Components of the compensation device according to at least one embodiment of the invention may predominantly be embodied as software components. In principle, however, some of these components may also be realized in the form of software-supported hardware, for example FPGAs or similar, in particular when particularly fast calculations are called for. Likewise, the required interfaces may be embodied as software interfaces, for example if all that needs to be done is to take over data from other software components. However, they may also be embodied as hardware interfaces that are controlled by suitable software.

In particular, the compensation device according to at least one embodiment of the invention may be part of a user terminal of a tomosynthesis device.

Realization in a largely software form has the advantage that it is also possible to retrofit compensation devices that have already been in use with a software update in a simple manner, such that they operate in an inventive manner. Thus, at least one embodiment is directed to a computer program product having a computer program that may be loaded directly into a storage device of a compensation device of a tomosynthesis device and has program portions, in order to carry out all the steps of the method according to at least one embodiment of the invention when the program is executed in the compensation device. A computer program product of this kind may include, in addition to the computer program, where appropriate additional constituent parts such as documentation and/or additional components, and hardware components such as hardware keys (dongles, etc.) for utilizing the software.

For the purpose of transport to the compensation device and/or storage on or in the compensation device there may serve a computer-readable medium such as a memory stick, a fixed disk or another portable or permanently installed data medium on which it is possible to store the program portions of the computer program that are to be read from a processor unit to the compensation device and executed. For this purpose, the processor unit may have for example one or more cooperating microprocessors or similar.

Further particularly advantageous embodiments and developments of the invention become apparent from the claims and the description below, wherein the independent claims of one category of claim may also be developed in a manner analogous to the dependent claims or parts of the description of another category of claim, and in particular individual features of different example embodiments or variants may also be combined to form new example embodiments or variants.

Preferably, when the adaptation of the reconstruction is carried out, the weightings of the X-ray sources and the weightings of the projection images acquired by the individual X-ray sources are redistributed. That is to say that, for the purpose of compensating for the X-ray source that is not functioning or is now only partly functioning, whereof the projection images are no longer used or are only partly used in determining the result image, the fully functional X-ray sources are given greater weighting.

Particularly preferably, the functional X-ray sources that are arranged adjacent to the faulty X-ray sources are given greater weighting. Most particularly preferably, the functional X-ray sources that are directly adjacent to the faulty X-ray sources are given even greater weighting than the other functional X-ray sources.

Further preferably, indirectly adjacent X-ray sources—where for example one, two or more functional X-ray sources are arranged between these and the faulty X-ray source—may be weighted to a correspondingly greater extent.

As a result of the greater weighting of adjacent X-ray sources, it is advantageously possible to compensate for an angular range that is represented to a lesser extent in the reconstruction because of the faulty X-ray source.

The term "X-ray stream" designates an electron stream that, for the purpose of generating X-ray radiation, is accelerated from a cathode of the X-ray sources to an anode of the X-ray sources and, as a result of interacting with the material of the anode, generates X-ray radiation in an X-ray spectrum. The X-ray stream and a tube voltage applied between the cathode and the anode generally define the intensity of X-ray imaging and hence the intensity of the projection images. Thus, the X-ray streams of the functional X-ray sources are preferably boosted in order advantageously to obtain projection images and thus also a result image that have the same intensity as in the case of regular acquisition. Here, the concept of "boosting the X-ray streams" means that their parameter values are adjusted to be higher for image acquisition, wherein image acquisition is not part of the method.

Particularly preferably, the X-ray streams are boosted in dependence on the number of faulty X-ray sources. That is to say that the more faulty or failed X-ray sources there are, the greater the extent to which the X-ray streams of the functional X-ray sources are boosted.

Most particularly preferably, the X-ray streams of the X-ray sources that are arranged adjacent to the faulty X-ray source are boosted to a greater extent. As explained above, the X-ray streams of indirect neighbors of the faulty X-ray sources may also be boosted.

As mentioned above, the intensity of the X-ray imaging is also defined, among other things, by the tube voltage. In order to keep the intensity of imaging the same even when there is a faulty X-ray source, the tube voltages of the functional X-ray sources are thus preferably increased. In this context, however, the extent to which increasing the tube voltage also brings about a shift in the X-ray spectrum that may have an undesirable effect on imaging has to be evaluated. The tube voltages are thus increased in particular if a boost to the X-ray radiation is not possible for other reasons. Here too, the concept of "increasing the tube voltage" means that their parameter values are adjusted to be higher for image acquisition, wherein image acquisition is not part of the method.

As described above with reference to the weighting of the X-ray sources or boosting of the X-ray stream, particularly preferably the X-ray voltage is also increased if there are adjacent X-ray sources, that is to say X-ray sources that are in particular directly and/or indirectly adjacent.

Preferably, a total dose is kept the same, as in the case of a regular examination using a fully functional tomosynthesis device. That is to say that the X-ray intensity is preferably adjusted by way of the respective above-described boosting of the X-ray stream and/or increasing of the tube voltage of the individual functional X-ray sources such that it corresponds to the dose acting on an object undergoing examination in the case of regular examination.

Preferably, an item of fault information relating to the detected faulty X-ray source is generated. The fault information or the error message is particularly preferably transmitted over a network. As already explained above, as a result service staff may be informed and/or examinations with higher demands may be reallocated to imaging on other modalities.

FIG. 1 shows, by way of example and in rough schematic terms, a tomosynthesis system 40 according to the invention that includes an example embodiment of a tomosynthesis device 30 according to the invention. The tomosynthesis device 30 has an X-ray source arrangement 31 in the form of a matrix, with a field of X-ray sources 36, 36'. In the X-ray source arrangement 31 there are for example three rows and a plurality of columns having a plurality of X-ray sources 36, 36'. The X-ray source arrangement 31 may also be curved inward.

Moreover, the tomosynthesis device 30 has a detector 32 by which the X-ray source arrangement 31 may be connected to a frame (not explicitly illustrated here) in stationary manner. Between the X-ray source arrangement 31 and the detector 32 there is, for the purpose of examination, an object undergoing examination O, such as the breast of a patient. The stationary X-ray sources 36, 36' are in this case aligned on a focus point FP in the object undergoing examination O.

In operation, the X-ray sources 36 each successively transmit X-ray radiation S in an acquisition step, which is not part of the method according to the invention. The X-ray radiation S passes through the object undergoing examination O and is detected by the detector 32 individually for each X-ray source 36, as a projection image PA (see FIG. 2).

The arrangement has the advantage that there is no need for any mechanical movement of X-ray tubes 36, 36' and/or the detector 32, and so there is no blurring of the focus that lessens the resolution of the images.

Further, the tomosynthesis device 30 includes a controller 20 and a reconstruction unit 33. The X-ray source arrangement 31, the detector 32, the controller and the reconstruction unit 33 are for example connected by way of a common bus 34 for the purpose of exchanging data. The exchanged data here may include for example control data, check data, and/or the data from the projection images PA that are detected by the detector 32.

The controller 20 has, in addition to further components (not illustrated here) that are conventional for controlling a tomosynthesis device, among other things a detection unit 23, a tube voltage regulating unit 25, an X-ray stream regulating unit 26, and an interface 21. The individual components of the controller 20 are in this case connected to one another by way of an internal bus 22 for the purpose of exchanging data; a connection with the other components of the tomosynthesis device 30 is made via the interface 21.

Here, the reconstruction unit 33 includes an integrated adaptation unit 24. It should be pointed out that the spatial or structural arrangement of the controller 20, the reconstruction unit 33 and the adaptation unit 24 is variable according to the invention provided that data exchange can take place between the individual components. Thus, the arrangement may for example be highly integrated—in other words be realized for example in a single processor unit. In another variant, the arrangement may also be decentralized, so for example the X-ray sources 36, 36' and the detector 32 may be arranged in one examination room but the controller 20 may be arranged in a separate control room. Functioning of the individual components 23, 24, 25, 26 will be explained below with reference to FIG. 2.

The controller 20, the reconstruction unit 33 and the adaptation unit 24 included therein together form an example embodiment of a compensation device 37 according to the invention.

Further, the tomosynthesis system 40 has a terminal 35, which is embodied for example for a user to input control criteria. A result image EB determined using the method according to an embodiment of the invention may for example also be output at the terminal 35. Moreover, the tomosynthesis system 40 includes a connection 41 to an external network such as a clinical network or the Internet, over which an item of fault information FI, output for example by the detection unit 23 of the controller 20, may be transmitted.

Figure 2:
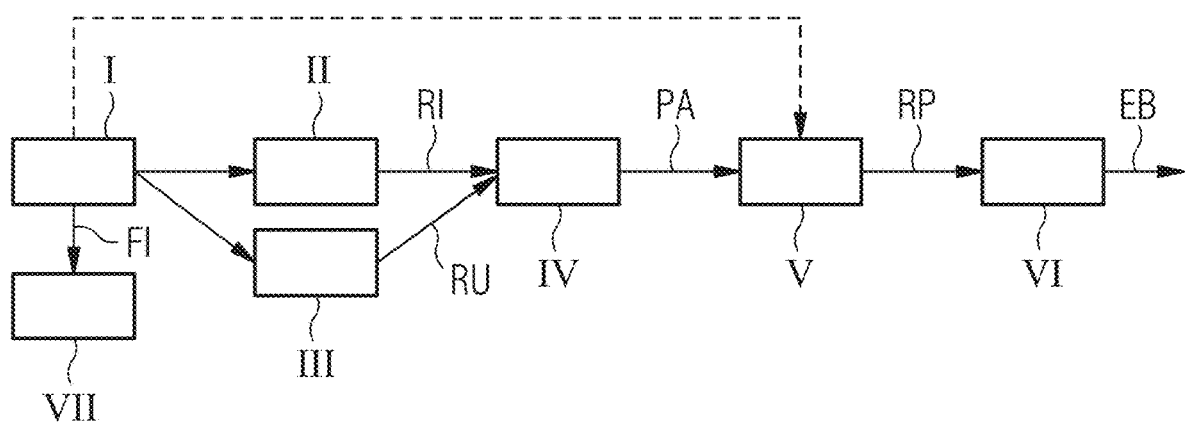
FIG. 2 shows a block diagram of an example embodiment of a method according to the invention for generating a result image.

FIG. 2 illustrates schematically, as a block diagram, an example embodiment of a method according to the invention for generating a result image EB.

In a first step I, a faulty—that is to say not fully functional—X-ray source 36' is detected via the detection unit 23. This may be performed for example by way of an irregular drop in voltage that is identified in the course of a resistance measurement. On detection of the faulty.

X-ray source 36', it is also possible at the same time to determine its position and functional X-ray sources 36 that are adjacent thereto.

In a further step II, values for the X-ray streams RI of the adjacent functional X-ray sources 36 that are higher than the values used in regular operation are determined. The values for the X-ray streams RI may be transmitted, for a subsequent acquisition step IV that is not part of the method according to the invention, to the X-ray sources 36 for operation thereof as control parameter values, via the X-ray stream regulating unit 26.

In a step III, values for the tube voltages RU of the adjacent functional X-ray sources 36 are determined that are the same as or higher than the values used in regular operation. They may also be transmitted, for the acquisition step IV, to the X-ray sources 36 for operation thereof as control parameter values, via the tube voltage regulating unit 25.

The tube voltages RU and the X-ray streams RI are determined in a mutually dependent manner, preferably in dependence on the number and/or position of the faulty X-ray sources 36', in order to achieve an X-ray intensity and total dose as usual in a regular examination. Here, in particular the X-ray streams RI and the tube voltages RU of X-ray sources 36 adjacent to the faulty X-ray sources 36' are respectively boosted and increased. This may advantageously compensate for the projection image PA of the faulty X-ray source 36', which in this angular range is not or not sufficiently acquired.

In an acquisition step IV, which is not part of the method according to the invention, the detector 32 detects a projection image PA of the object undergoing examination O for each of the X-ray sources 36, which are activated successively and in any desired order. The acquisition of such projection images per is well known to those skilled in the art and will not therefore be described in more detail.

In a further step V, the reconstruction is adapted via the adaptation unit 24 for the purpose of compensating for the faulty X-ray source 36'. That is to say that parameter values, such as in particular weighting of the individual projection images PA, are varied such that the result image EB corresponds as far as possible to that of regular imaging. In the course of this step V, it is also possible for a specific reconstruction method for generating the result image EB to be selected, and/or for pre- or post-processing steps to be performed, in order as a result to achieve imaging that is regular as far as possible. All these adaptations may be grouped for example under the term "reconstruction parameter values" RP, and may be stored as such and retrieved or transmitted for the purpose of a reconstruction that is as appropriate carried out later or at a different location.

In a step VI, the actual reconstruction of the result image EB is performed on the basis of the projection images PA using the reconstruction unit 33, wherein the reconstruction is carried out using adaptations determined step V or using the reconstruction parameter values RP. Here, the result image EB may be generated for example in the form of a volume image or a layered image stack and/or in the form of a synthetic mammogram. The fundamental procedure of a reconstruction is known, so a detailed description will be dispensed with.

In a further step VII, the controller 20 or the tomosynthesis system may output to a network an item of fault information FI relating to the faulty or defective X-ray source 36', via an interface or connection 41. The fault information FI may where appropriate additionally include an item of information on the device location. It may for example be forwarded to service staff who can arrange for an overhaul of the device, depending on the number of defective X-ray sources and the device location.

As an alternative or in addition, on the basis of the fault information FI a reallocation of upcoming examinations may be performed by a hospital planning system. Here, examinations that make higher demands of imaging may for example be reallocated to other modalities, wherein the demands of imaging may be determined for example on the basis of the clinical picture and/or the patient's file. This enables more efficient utilization of the modalities to be ensured, with sufficiently high quality of the image material for useful findings being maintained to the greatest possible extent.

It is thus possible, using the method according to an embodiment of the invention for generating a result image, to substantially compensate for the effects of faulty or failed X-ray sources, with the result that advantageously shorter down times can be achieved in the tomosynthesis device or system. On the one hand this enables savings on costs that would arise from the procurement of additional modalities for reasons of redundancy, and on the other it is possible to ensure a seamless procedure when utilizing the tomosynthesis device.

Finally, it should be pointed out again that the devices and methods described in detail above are merely example embodiments, which may be modified by those skilled in the art in the greatest variety of ways without departing from the scope of the invention. Thus, for example, only a mammography system is described above, but the invention may in principle relate to any X-ray system with a combined X-ray and 3D ultrasound device. Furthermore, the use of the indefinite articles "a" and "an" does not rule out the possibility that the features concerned may also be present a plurality of times. Likewise, the terms "device", "arrangement" and "system" do not rule out the possibility that the component concerned comprises a plurality of cooperating partial components, which where appropriate may also be spatially separated from one another.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for generating a result image using a tomosynthesis device including a plurality of stationary X-ray sources, the method comprising:
    detecting a faulty X-ray source among the plurality of stationary X-ray sources;
    generating a first projection image;
    adapting a reconstruction to compensate for the faulty X-ray source by varying a first weighting of the first projection image to be higher than a second weighting of a second projection image, the second weighting to be higher than a third weighting of a third projection image and a fourth weighting of a fourth projection image to be lower than the third weighting, the fourth projection image corresponding to the faulty X-ray source; and
    generating the result image using the reconstruction.

2. The method of claim 1, wherein each of the first weighting, the second weighting, the third weighting and the fourth weighting corresponds to a different one among the plurality of stationary X-ray sources.

3. The method of claim 1, further comprising:
    boosting a plurality of X-ray streams of a plurality of functional X-ray sources among the plurality of stationary X-ray sources in response to the detecting.

4. The method of claim 3, wherein the boosting boosts a first of the plurality of X-ray streams to a greater extent than a second of the plurality of X-ray streams, the first of the plurality of X-ray streams being from a first of the plurality of functional X-ray sources, and the first of the plurality of functional X-ray sources being adjacent to the faulty X-ray source.

5. The method of claim 3, wherein the boosting includes increasing a plurality of tube voltages of the plurality of functional X-ray sources.

6. The method of claim 3, wherein a total dose is kept constant.

7. The method of claim 1, further comprising:
    generating fault information.

8. A non-transitory computer-readable medium storing a computer program that is directly loadable into a storage device of a compensation device including at least one processor, the computer program including program portions to carry out the method of claim 1 when the computer program is executed by the at least one processor.

9. A non-transitory computer-readable medium storing program portions, readable from and executable by at least one processor, to carry out the method of claim 1 when the program portions are executed by the at least one processor.

10. The method of claim 2, further comprising:
boosting a plurality of X-ray streams of a plurality of functional X-ray sources among the plurality of stationary X-ray sources.

11. The method of claim 10, wherein the boosting boosts a first of the plurality of X-ray streams to a greater extent than a second of the plurality of X-ray streams, the first of the plurality of X-ray streams being from a first of the plurality of functional X-ray sources, and the first of the plurality of functional X-ray sources being adjacent to the faulty X-ray source.

12. The method of claim 1, further comprising:
increasing a plurality of tube voltages of a plurality of functional X-ray sources among the plurality of stationary X-ray sources.

13. The method of claim 2, further comprising:
increasing a plurality of tube voltages of a plurality of functional X-ray sources among the plurality of stationary X-ray sources.

14. The method of claim 4, wherein a total dose is kept constant.

15. The method of claim 5, wherein a total dose is kept constant.

16. The method of claim 7, further comprising:
causing the fault information to be transmitted over a network.

17. The method of claim 1, wherein each of the plurality of stationary X-ray sources corresponds to a different detected projection image among a plurality of detected projection images, the plurality of detected projection images including the first projection image.

18. The method of claim 1, wherein
the first projection image corresponds to a functional X-ray source among the plurality of stationary X-ray sources; and
the first weighting of the first projection image includes first weighting the first projection image according to a proximity of the functional X-ray source to the faulty X-ray source.

19. The method of claim 1, wherein the second projection image corresponds to a functional X-ray source among the plurality of stationary X-ray sources, the functional X-ray source not being adjacent to the faulty X-ray source.

20. A compensation device, comprising:
at least one processor configured to execute computer readable instructions to cause the compensation device to
detect a faulty X-ray source among a plurality of stationary X-ray sources,
generate a first projection image,
adapt a reconstruction to compensate for the faulty X-ray source by varying a first weighting of the first projection image to be higher than a second weighting of a second projection image, the second weighting to be higher than a third weighting of a third projection image and a fourth weighting of a fourth projection image to be lower than the third weighting, the fourth projection image corresponding to the faulty X-ray source, and
generate a result image using the reconstruction.

21. A tomosynthesis device comprising:
the plurality of stationary X-ray sources; and
the compensation device of claim 20.

22. A tomosynthesis system comprising:
a terminal configured to output the result image; and
the tomosynthesis device of claim 21.

23. A tomosynthesis device, comprising:
a plurality of X-ray sources; and
a compensation device including
a detector configured to detect a faulty X-ray source among the plurality of X-ray sources, and
at least one processor configured to execute computer-readable instructions to
generate a first projection image,
adapt a reconstruction to compensate for the faulty X-ray source by varying a first weighting of the first projection image to be higher than a second weighting of a second projection image, the second weighting to be higher than a third weighting of a third projection image and a fourth weighting of a fourth projection image to be lower than the third weighting, the fourth projection image corresponding to the faulty X-ray source, and
generate a result image using the reconstruction.

* * * * *